US00PP14023P29

(12) United States Plant Patent
Kientzler

(10) Patent No.: US PP14,023 P2
(45) Date of Patent: Jul. 29, 2003

(54) NEW GUINEA IMPATIENS PLANT NAMED 'KIADIME'

(75) Inventor: Ludwig Kientzler, Gensingen (DE)

(73) Assignee: Innovaplant GmbH + Co. KG, Gensingen (DE)

( * ) Notice: Subject to any disclaimer, the term of this patent is extended or adjusted under 35 U.S.C. 154(b) by 0 days.

(21) Appl. No.: 10/158,962

(22) Filed: May 31, 2002

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Kiadime', characterized by its rounded, upright and compact plant habit; freely branching growth habit; bushy appearance; variegated foliage; freely flowering habit with flowers held above and beyond the foliage; and red purple-colored flowers.

1 Drawing Sheet

BOTANICAL CLASSIFICATION/CULTIVAR DESIGNATION

*Impatiens hawkeri* cultivar Kiadime.

BACKGROUND OF THE INVENTION

The present Invention relates to a new and distinct cultivar of New Guinea Impatiens plant, botanically known as *Impatiens hawkeri*, and hereinafter referred to by the cultivar name Kiadime.

The new Impatiens is a product of a planned breeding program Inventor in Gensingen, Germany. The objective of the breeding program is to develop new Impatiens cultivars with interesting and unique flower and foliage colors.

The new Impatiens originated from a cross-pollination made by the Inventor in October, 1998 of a proprietary *Impatiens hawkeri* selection identified as 97-283, not patented, as the female, or seed parent, with a proprietary *Impatiens hawkeri* selection identified as 97-515, not patented, as the male, or pollen parent. The cultivar Kiadime was discovered and selected by the Inventor as a flowering plant within the progeny of the stated cross-pollination in a controlled environment in Gensingen, Germany in March, 1999.

Asexual reproduction of the new cultivar by terminal cuttings taken at Gensingen, Germany, since May, 1999, has shown that the unique features of this new Impatiens are stable and reproduced true to type in successive generations.

SUMMARY OF THE INVENTION

The following traits have been repeatedly observed and are determined to be the unique characteristics of 'Kiadime'. These characteristics in combination distinguish 'Kiadime' as a new and distinct Impatiens cultivar:

1. Rounded, upright and compact plant habit.
2. Freely branching growth habit; bushy appearance.
3. Variegated foliage.
4. Freely flowering habit with flowers held above and beyond the foliage.
5. Red purple-colored flowers.

Plants of the new Impatiens differ from plants of the female parent, the selection 97-283, in the following characteristics:

1. Plants of the new Impatiens and plants of the selection 97-283 differ in leaf coloration.
2. Plants of the new Impatiens have more rounded flowers than plants of the selection 97-283.

Plants of the new Impatiens differ from plants of the male parent, the selection 97-515, primarily in leaf coloration as plants of the selection 97-515 do not have variegated leaves.

Plants of the new Impatiens can be compared to plants of the cultivar Kinoc, disclosed in U.S. Plant Pat. No. 10,433. In side-by-side comparisons conducted in Gensingen, Germany, plants of the new Impatiens differed from plants of the cultivar Kinoc primarily in leaf coloration as plants of the cultivar Kinoc did not have variegated leaves.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Impatiens. The photograph comprises a side perspective view of three typical flowering plants of 'Kiadime' grown in a 22-cm container.

DETAILED BOTANICAL DESCRIPTION

The cultivar Kiadime has not been observed under all possible environmental conditions. The phenotype may vary somewhat with variations in environment such as temperature and light intensity, without, however, any variance in genotype. The aforementioned photograph and the following observations and measurements describe plants grown in Encinitas, Calif., during the late spring, under commercial practice in a polyethylene-covered greenhouse with day temperatures about 24° C., night temperatures about 18° C., and light levels typically about 4,000 foot-candles. Plants used in the photograph and following description were about 14 weeks old and grown in 22-cm containers with three plants per container.

In the following description, color references are made to The Royal Horticultural Society Colour Chart, 1995 Edition, except where general terms of ordinary dictionary significance are used.

Botanical classification: *Impatiens hawkeri* cultivar Kiadime.

Parentage:

*Female, or seed, parent.*—Proprietary *Impatiens hawkeri* selection identified as 97-283, not patented.

*Male, or pollen, parent.*—Proprietary *Impatiens hawkeri* selection identified as 97-515, not patented.

Propagation:

*Type cutting.*—Terminal cuttings.

*Time to initiate roots.*—Summer: About 14 days at 23° C. Winter: About 17 days at 20° C.

*Time to produce a rooted cutting or liner.*—Summer: About 21 days at 23° C. Winter: About 24 days at 20° C.

*Root description.*—Fine, fibrous, and freely branching.

Plant description:

*General appearance.*—Rounded and somewhat upright; compact. Appropriate for 10 to 25-cm containers; multiple plants are typically planted in larger containers.

*Growth and branching habit.*—Freely branching with about nine lateral branches developing at the base, dense and bushy growth. Pinching, that is, removal of the terminal apices, is typically not required. Moderately vigorous.

*Plant height.*—About 20 cm.

*Plant diameter, single plant.*—About 15 cm.

*Lateral branches.*—Length: About 10 cm. Diameter: About 7 mm. Internode length: About 3.5 cm. Texture: Sparsely pubescent. Color: 185A.

*Foliage description.*—Arrangement: Opposite or in whorls; simple. Length: About 10 cm. Width: About 3.8 cm. Shape: Elliptic. Apex: Acute. Base: Attenuate. Margin: Serrulate with ciliation. Texture, upper surface: Slightly pubescent. Texture, lower surface: Smooth, glabrous. Color: Young foliage, upper surface: Towards margin, darker than 147A; towards center, 34B; center, 20A. Young foliage, lower surface: 59A to 59B. Fully expanded foliage, upper surface: Towards margin, darker than 147A; towards center, 39B to 39C; center, 27A. Fully expanded foliage, lower surface: 42A to 42B. Venation, upper surface: 50B. Venation, lower surface: 53A. Petiole: Length: About 4 cm. Diameter: About 4 mm. Texture, upper and lower surfaces: Smooth, glabrous. Color, upper and lower surfaces: 63A.

Flower description:

*Flower type and flowering habit.*—Single axillary flowers. Freely flowering, usually about eight flowers and flower buds per lateral branch. Flowers typically face upward or outward and held above and beyond the foliage. Flowers somewhat cupped and rounded in shape. Flowers last about eight days on the plant depending on temperature and weather conditions. Petals self-cleaning; gynoecium persistent. Flowers not fragrant.

*Flowering season.*—Year-round under greenhouse conditions. In the garden, flowering from spring until fall.

*Flower height.*—About 4.5 cm.

*Flower width.*—About 4.5 cm.

*Flower depth.*—About 2 cm.

*Flower buds* (*at stage of showing color*).—Rate of opening: From showing color to fully open flower, typically about 2 to 3 days depending on temperature. Length: About 1.6 cm. Diameter: About 8 mm. Shape: Ovoid. Color: 53A to 53B.

*Petals.*—Quantity: Single, five per flower. Length: Banner petal: About 2.3 cm. Lateral petals: About 2.7 cm. Base petals: About 3 cm. Width: Banner petal: About 3.7 cm. Lateral petals: About 2.8 cm. Base petals: About 3.3 cm. Shape: Cordate. Apex: Emarginate. Base: Acute. Margin: Entire. Texture: Smooth; velvety. Color: When opening, upper surface: Slightly brighter than 58A. When opening, lower surface: 58C; towards base, 50A. Fully opened, upper surface: 61C; towards base, 50A; color becoming closer to 46B with subsequent development. Fully opened, lower surface: 52C; towards base, 50A to 50B.

*Spur.*—Length: About 4.5 cm. Texture: Smooth, glabrous. Color: 53C.

*Peduncles.*—Length: About 3.7 cm. Diameter: About 1 mm. Strength: Strong. Angle: About 45° from vertical. Texture: Smooth, glabrous. Color: 185B.

*Reproductive organs.*—Androecium: Stamen number: Five fused at anthers, filaments free. Anther shape: Obovate. Anther size: About 4 mm by 5 mm. Anther color: 23C. Amount of pollen: Moderate. Pollen color: 158B. Gynoecium: Pistil length: About 5 mm. Stigma color: 59A. Style color: 144A overlain with 59B. Ovary color: 144A overlain with 59B.

*Seed/fruit.*—Seed and fruit development has not been observed.

Disease/pest resistance: Plants of the new Impatiens have not been observed to be resistant to pathogens and pests common to Impatiens.

Temperature tolerance: Plants of the new Impatiens have been observed to tolerate temperatures from 16 to 30° C.

It is claimed:

1. A new and distinct cultivar of New Guinea Impatiens plant named 'Kiadime', as illustrated and described.

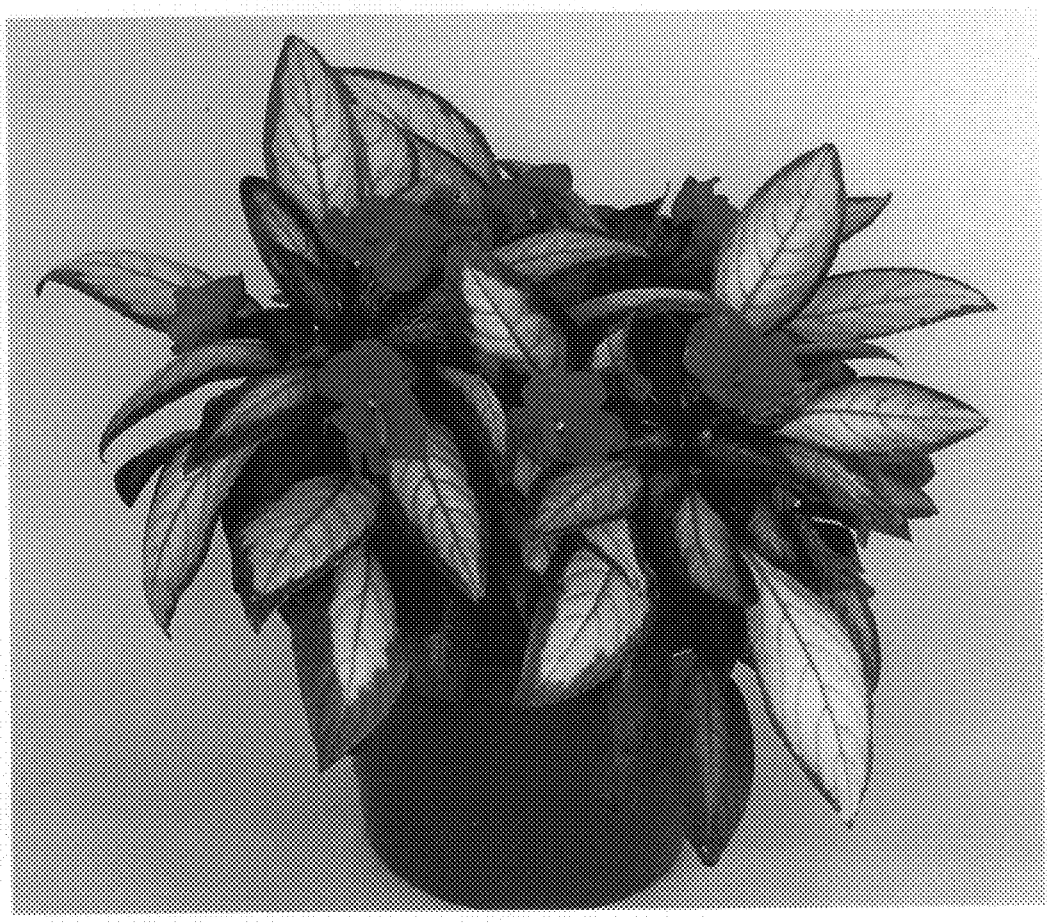

* * * * *